United States Patent
Schubert et al.

(10) Patent No.: US 7,268,241 B2
(45) Date of Patent: *Sep. 11, 2007

(54) METHOD FOR THE PRODUCTION OF 4-(17$G(A)-METHYL SUBSTITUTED 3-OXOESTRA-4 9-DIEN-11$G(B)-YL)BENZALDEHYD-(1E OR 1Z)-OXIMES

(75) Inventors: Gerd Schubert, Jena (DE); Sven Ring, Jena (DE); Bernd Erhart, Kahla (DE); Gerd Mueller, Jena (DE)

(73) Assignee: Schering AG, Berlin (DE)

( * ) Notice: Subject to any disclaimer, the term of this patent is extended or adjusted under 35 U.S.C. 154(b) by 694 days.

This patent is subject to a terminal disclaimer.

(21) Appl. No.: 10/416,234

(22) PCT Filed: Nov. 9, 2001

(86) PCT No.: PCT/DE01/04217

§ 371 (c)(1), (2), (4) Date: Oct. 24, 2003

(87) PCT Pub. No.: WO02/38581

PCT Pub. Date: May 16, 2002

(65) Prior Publication Data

US 2004/0063172 A1  Apr. 1, 2004

(30) Foreign Application Priority Data

Nov. 10, 2000  (DE) .................. 100 56 675

(51) Int. Cl.
*C07J 1/00* (2006.01)
(52) U.S. Cl. .................................... 552/648
(58) Field of Classification Search .......... 552/648
See application file for complete search history.

(56) References Cited

U.S. PATENT DOCUMENTS 5,693,628 A    12/1997   Schubert et al.

FOREIGN PATENT DOCUMENTS

DE    289539    *   5/1991
EP    0648778       4/1995

* cited by examiner

*Primary Examiner*—Barbara P. Badio
(74) *Attorney, Agent, or Firm*—Millen, White, Zelano & Branigan, P.C.

(57) ABSTRACT

The invention relates to a process for the production of 4-(17α-methyl-substituted 3-oxoestra-4,9-dien-11β-yl)benzaldehyde-(1E or 1Z)-oximes of general formula (I), in which $R_1$ is a hydrogen atom, a $C_{1-6}$-alkyl radical or a $C_nF_{2n+1}$ radical, whereby n is 1, 2 or 3, $R_2$ is a $C_{1-4}$-alkyl radical, X is an OH group in E- or Z-position, and Y is an $OC_{1-6}$-alkyl group, an $SC_{1-6}$-alkyl group or an $OCH_2C_nF_{2+1}$ group, whereby n is 1, 2 or 3, which provides the target compounds of formula (I) with a high yield and good selectivity

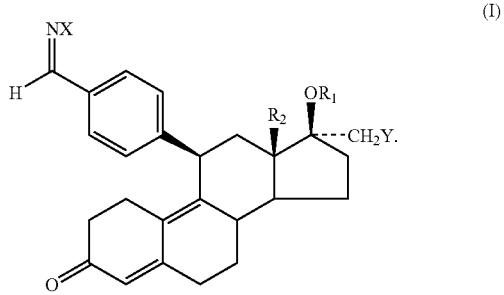

(I)

20 Claims, No Drawings

METHOD FOR THE PRODUCTION OF 4-(17$G(A)-METHYL SUBSTITUTED 3-OXOESTRA-4 9-DIEN-11$G(B)-YL)BENZALDEHYD-(1E OR 1Z)-OXIMES

This application is a National Stage Application of PCT/DE01/04217, filed on Nov. 9, 2001, and claims priority to DE 100 56 675.8, filed on Nov. 10, 2000.

The invention relates to a process for the production of 4-(17α-methyl-substituted 3-oxoestra-4,9-dien-11β-yl)benzaldehyde-(1E or 1Z)-oximes of general formula (I)

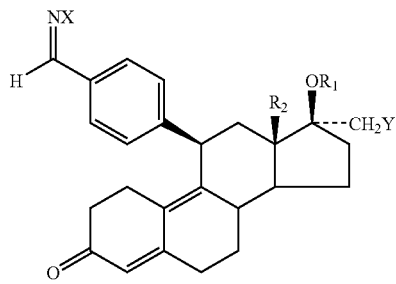

(I)

in which $R_1$ is a hydrogen atom, a $C_{1-6}$-alkyl radical or a $C_nF_{2n+1}$ radical, whereby n is 1, 2 or 3, $R_2$ is a $C_{1-4}$-alkyl radical, X is an OH group in E- or Z-position, and Y is an $OC_{1-6}$-alkyl group, $SC_{1-6}$-alkyl group or an $OCH_2C_nF_{2n+1}$ group, whereby n is 1, 2 or 3.

4-(17α-Methyl-substituted 3-oxoestra-4,9-dien-11β-yl)benzaldehyde-(1E or 1Z)-oximes are already known. Substances of this type are described in DE 4332283 A1 (EP 0 648 778 B1). Because of the advantageous antigestagenic action and slight antiglucocorticoidal action, the compounds are of general interest for treating a number of hormone-dependent female diseases, such as, for example, endometriosis.

The existing process for their production preferably uses as a starting material 5α, 10α-epoxy-estr-9(11)-en-17-one of formula (II) that is protected as a dimethyl ketal on a C-3 as a ketal

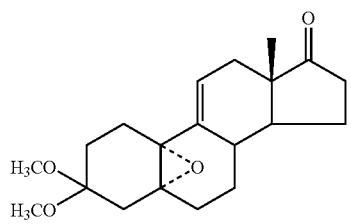

(II)

In a first step, in a way that is known in the art, the 5α,10α-epoxide of formula (II) is opened by a Cu(I)-salt-catalyzed Grignard reaction with a 4-bromobenzaldehyde ketal, preferably the 4-bromobenzaldehyde dimethyl ketal, to 11β-aryl-substituted 5α-hydroxy steroids of formula (III)

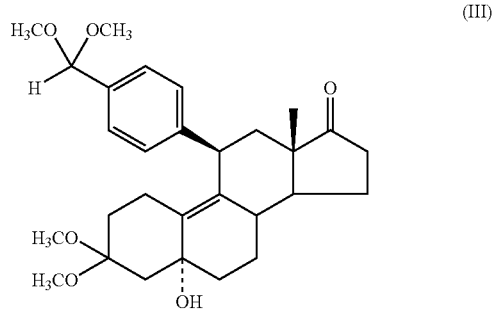

(III)

In this case, the yield of the process is not optimal since a portion (3 to 10%) of the 17-oxo group is also attacked, whereby 11β, 17α-bisaryl-substituted steroids of formula (IV)

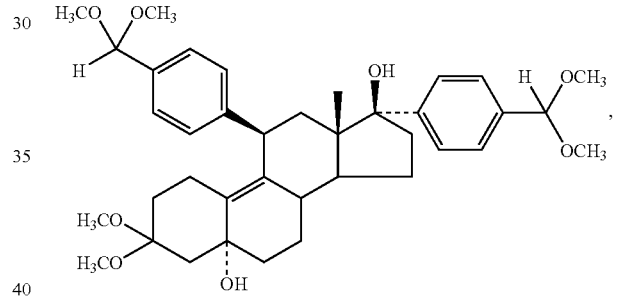

(IV)

that are very expensive to separate by chromatography from the desired 11β-monoaryl-substituted compounds of formula (III) are produced.

According to COREY and CHAYKOWSKY (J. Amer. Chem. Soc. 84, 3782 [1962]), the mixture of the compounds of formulas (E) and (IV) is converted mainly into the spiroepoxide of formula (V)

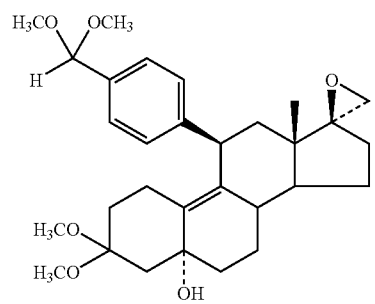

(V)

which is opened by alkali methylate to a 17α-methoxy compound of formula (VI)

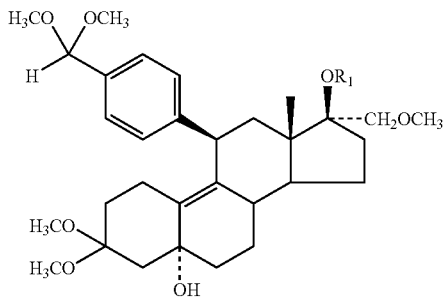

in which $R_1$ is a hydrogen atom. The compound of formula (IV) is converted either immediately or after etherification of the 17β-hydroxyl group with alkyl halides in the presence of bases into compounds of general formula (VI), in which $R_1$ is a $C_{1-6}$-alkyl radical, by acid hydrolysis in the benzaldehydes of formula (VII)

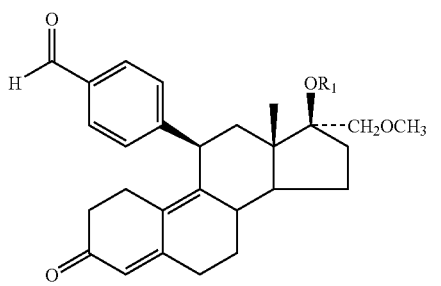

in which $R_1$ is a hydrogen atom or a $C_{1-6}$-alkyl radical. The 11β,17β-bisaryl steroids of formula (IV) that are produced in the Grignard reaction as by-products are constantly entrained under the above-mentioned conditions and ultimately hydrolyzed to the bisaldehydes of formula (VIII)

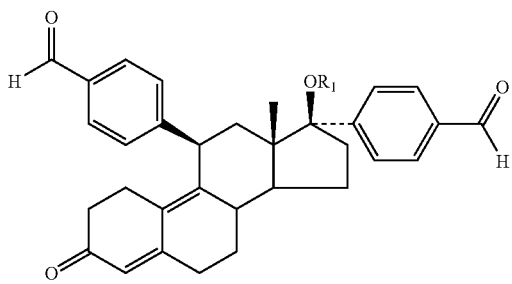

These bisaldehydes of formula (VIII) differ in the crystallization behavior and in their chromatographic properties only slightly from the monoaldehydes of formula (VII) and are difficult to separate quantitatively and thus pose a problem in the production of the compounds of formula (I) according to the invention.

The object of this invention is therefore to make available a technically simpler and more effective process for the production of 4-(17α-methyl-substituted 3-oxoestra-4,9-dien-11β-yl)benzaldehyde-(1E or 1Z)-oximes of formula (I) that prevents the attack of the Grignard compound on the C-17 and produces the target compounds of formula (I) with higher yield and better selectivity.

This object is achieved according to the process of claim 1.

Since the 17-keto group is converted into the desired 17α-methyl-substituted compound before the grignardization, the formation of the by-product of formula (VIII) can be prevented, by which the target compounds are obtained with higher yield and purity. Thus, for example, using compound (II) as a starting material according to the process of DE 43 32 283 A1, aldehyde (VIIb) can be produced at a yield of about 5.6% and accordingly oxime (Ic) can be produced at a yield of about 3.8%. By the process according to the invention, aldehyde (VIIb) can now be produced at a yield of about 33% or oxime (Ic) can be produced at a yield of about 23% from olefin (IX), without special chromatographic conditions having to be used for the purification.

Preferred embodiments of the invention are indicated in the subclaims. Because of additional advantages of the invention, reference is made to the following description and the embodiments.

According to the invention, the 3,3-dimethoxy-estra-5(10),9(11)-en-17-one of formula (IX)

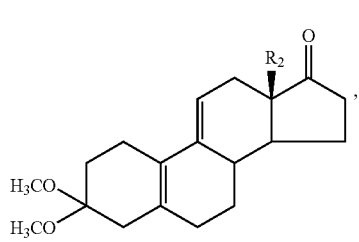

in which $R_2$ is a $C_{1-4}$-alkyl radical, is converted with an active methylene reagent, which is produced from, e.g., trimethylsulfonium iodide and a strong base, such as potassium-tert-butanolate, in solvents, such as DMSO, DMF or toluene, into the spiroepoxide of formula (X)

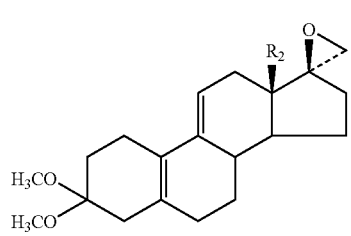

in which $R_2$ has the above-indicated meaning, and which, after cleavage of the 17-spiroepoxy group by alkali or alkaline-earth alcoholate, alkali or alkaline-earth thiolalcoholate or by trifluoroalkyl alcohols and potassium-tert-butanolate, preferably by sodium methanolate in solvents, such as methanol, DMF or DMSO, is opened to the 17α-CH$_2$—Y compound of formula (XI)

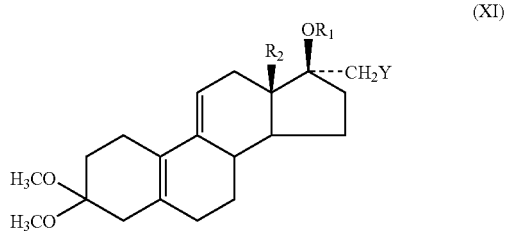

(XI)

in which R$_1$ represents a hydrogen atom, and R$_2$ has the above-indicated meaning, and Y is an OC$_{1-8}$-alkyl group, SC$_{1-6}$-alkyl group or an OCH$_2$C$_n$F$_{2+1}$ group, whereby n is 1, 2 or 3.

By reaction of the 17β-hydroxyl group with alkyl halides or fluoroalkyl halides (halogen=chlorine, bromine or iodine), such as fluoroalkyl iodide, in the presence of strong bases, such as potassium hydroxide, alcoholates, such as potassium-tert-butanolate, silver fluorides, alkali metals and naphthalene or biphenyl, in inert solvents, such as ethers, tetrahydrofuran (THF) or toluene, the 17β-ethers of formula (XI) are formed, in which R$_1$ is a C$_{1-6}$-alkyl radical or a C$_n$F$_{2n+1}$ radical, whereby n represents 1, 2 or 3, and R$_2$ and Y have the above-indicated meanings. The compounds of general formula (XI) are epoxidized in a regioselective manner on the 5(10)-double bond. The epoxidation with hydrogen peroxide and hexachloro- or hexafluoroacetone is carried out preferably in the presence of catalytic amounts of a tertiary amine, such as triethylamine or pyridine, whereby a mixture is produced from 5α,10α-epoxy- and 5β,10β-epoxy-17α-methyl-substituted estr-9(11)-ene-3,3-dimethyl ketal of formula (XII)

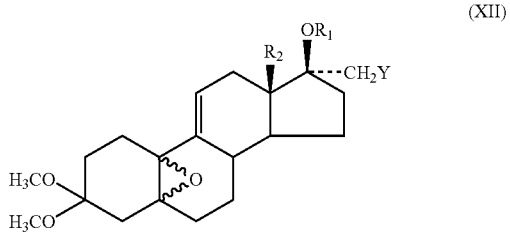

(XII)

in which R$_1$, R$_2$ and Y have the above-indicated meanings, which preferably is not separated into individual components but rather is opened directly with a 4-bromobenzaldehyde ketal, such as 4-bromobenzaldehyde dimethyl ketal, magnesium and Cu(I)Cl at temperatures of between −35° C. and room temperature to the corresponding 3,3-dimethoxy-5α-hydroxy-17α-(methyl-substituted 11α,β-benzaldehyde-dimethyl ketal of formula (XIII)

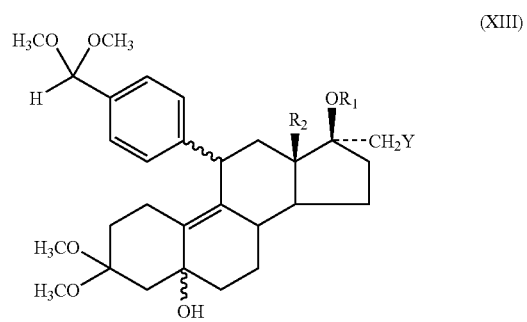

(XIII)

in which R$_1$, R$_2$ and Y have the above-indicated meaning. This mixture is preferably subjected immediately, without intermediate isolation, to acid hydrolysis to cleave the protective groups, for example with dilute acetic acid or p-toluenesulfonic acid, in solvents such as acetone or THF. In this case, a mixture of the 11α,β-benzaldehyde derivatives of formula (XIV) is produced

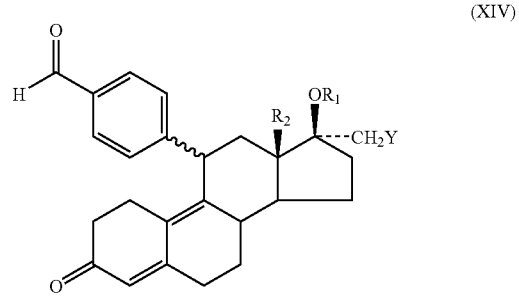

(XIV)

in which R$_1$, R$_2$ and Y have the above-indicated meanings, from which, surprisingly enough, the pure 11β-benzaldehydes are isolated by crystallization (That is, in the grignardization of the epoxide mixture, two isomeric compounds that differ only slightly in their chromatographic properties and should actually crystallize in a very similar way are produced on the C-11. Surprisingly enough, only the 11β-compound crystallizes out, since it is very poorly soluble. Thus, the extensive separation of the 11-α-aldehyde and simultaneously also the separation of the non-steroidal by-products are possible by an individual crystallization. This is especially important since these by-products would otherwise have an especially disruptive action because of the 4× excess of Grignard reagent and would be separable only by chromatography), in which R$_1$, R$_2$ and Y have the above-indicated meanings, and the aldehyde functions are converted by hydroxylammonium salts, preferably hydroxylamine hydrochloride, in the presence of bases, preferably pyridine, at room temperature in a mixture of the E/Z-benzaldoximes of general formula (I), in which R$_1$, R$_2$ and Y have the above-indicated meanings, and X means an OH group in E- or Z-position. The E/Z-benzaldoximes of general formula (I) can be separated by recrystallization and/or by chromatography, purified and isolated as individual components.

In this invention, "alkyl radical" is defined as a branched or straight-chain alkyl radical. As C$_{1-4}$- or C$_{1-6}$-alkyl radicals, for example, a methyl, ethyl, n-propyl, i-propyl, n-butyl, i-butyl or tert-butyl, n-pentyl, i-pentyl, n-hexyl, 2-methylpentyl, 3-methylpentyl, 2,2-dimethylbutyl or 2,3-dimethylbutyl group can be mentioned. A $C_nF_{2n+1}$ radical is defined as a branched or straight-chain fluoroalkyl radical with 1 to 3 carbon atoms, whereby examples are a trifluoromethyl, pentafluoroethyl, heptafluoro-n-propyl or heptafluoro-isopropyl group. $R_1$ and $R_2$ preferably mean a $C_{1-3}$-alkyl radical, especially preferably a methyl group or a trifluoromethyl group.

Y preferably means an $OC_{1-3}$-alkyl radical or an $SC_{1-3}$-alkyl radical, especially preferably a methoxy, ethoxy, isopropyloxy, methylthio or ethylthio group, or a trifluoroethoxy group. The compounds of formula (I), in which $R_1$ is a $C_nF_{2n+1}$ radical and/or Y is an $OCH_2C_nF_{2n+1}$ group, are new.

Most preferred within the framework of the compounds of formula (I) are the following compounds:

4-[17β-Hydroxy-17α-(methoxymethyl)-3-oxoestra-4,9-dien-11β-yl]benzaldehyde-1E-oxime, 4-[17β-Hydroxy-17α-(methoxymethyl)-3-oxoestra-4,9-dien-11β-yl]benzaldehyde-1Z-oxime, 4-[17β-Methoxy-17α-(methoxymethyl)-3-oxoestra-4,9-dien-11β-yl]benzaldehyde-1E-oxime, 4-[17β-Methoxy-17α-(methoxymethyl)-3-oxoestra-4,9-dien-11β-yl]benzaldehyde-1Z-oxime, 4-[17β-Ethoxy-17α-(methoxymethyl)-3-oxoestra-4,9-dien-11β-yl]benzaldehyde-1E-oxime, 4-[17β-Hydroxy-17α-(ethoxymethyl)-3-oxoestra-4,9-dien-11β-yl]benzaldehyde-1E-oxime, 4-[17β-Methoxy-17α-(ethoxymethyl)-3-oxoestra-4,9-dien-11β-yl]benzaldehyde-1E-oxime, 4-[17β-Hydroxy-17α-(isopropyloxymethyl)-3-oxoestra-4,9-dien-11β-yl]benzaldehyde-1E-oxime, 4-[17β-Methoxy-17α-(isopropyloxy-methyl)-3-oxoestra-4,9-dien-11β-yl]benzaldehyde-1E-oxime, 4-[17β-Hydroxy-17α-(ethylthiomethyl)-3-oxoestra4,9-dien-11β-yl]benzaldehyde-1E-oxime and 4-[17β-Hydroxy-17α-(1,1,1-trifluoroethoxymethyl)-3-oxoestra-4,9-dien-11β-yl]benzaldehyde-1E-oxime.

The compounds are well bonded to the gestagen receptor, show a strong antigestagenic activity in the animal experiment, have a partial gestagenic activity and exhibit only a slight gluococorticoid receptor binding [see Table 1 and cf. DE 43 32 283 A1 (EP 0 648 778 B1)].

Biological Characterization of the Compounds According to the Invention

The receptor binding affinity was determined by competitive binding of a specifically binding $^3$H-labeled tracer and the compound to be tested to receptors in the cytosol from animal target organs. In this case, receptor saturation and reaction equilibrium in the case of the following reaction conditions were sought:

Progesterone Receptor:

Uterus cytosol of the estradiol-primed rabbit, stored at −30° C., in TED buffer (20 mmol of Tris/HCl, pH 7.4; 1 mmol of ethylenediamine tetraacetate, 2 mmol of dithiothreitol) with 250 mmol of saccharose.

Tracer: $^3$H—ORG 2058

Reference substance: Progesterone

Glucocorticoid Receptor:

Thymus cytosol of the adrenalectomized rat, thymi stored at −30° C.; TED buffer

Tracer: $^3$H-Dexamethasone, 20 nmol

Reference substance: Dexamethasone

The early-abortive action was determined in the rat after subcutaneous administration from the 5th to the 7th day of pregnancy [administration 0.2 ml/animal/day in benzyl benzoate/castor oil (1+4 v/v)]. The dose indicates what amount must be given to at least 4 animals apiece in comparison to untreated animals, so that a complete inhibition of pregnancy is achieved.

TABLE 1

Receptor Binding of Selected Compounds

| Compound | Progesterone Receptor [Progesterone = 100%] | Glucocorticoid Receptor [Dexamethasone = 100%] | 100% Early-abortive Action in the Rat [mg/animal/day] |
|---|---|---|---|
| 4-[17β-Hydroxy-(17α-(methoxymethyl)-3-oxoestra-4,9-dien-11β-yl]benzaldehyde-1E-oxime | 165 | 76 | 1.0 |
| 4-[17β-Hydroxy-(17α-(methoxymethyl)-3-oxoestra-4,9-dien-11β-yl]benzaldehyde-1Z-oxime | 75 | 67 | 1.0 |
| 4-[17β-Methoxy-(17α-(methoxymethyl)-3-oxoestra-4,9-dien-11β-yl]benzaldehyde-1E-oxime | 302 | 78 | 1.0 |
| 4-[17β-Methoxy-17α-(methoxymethyl)-3-oxoestra-4,9-dien-11β-yl]benzaldehyde-1Z-oxime | 126 | 52 | 1.0 |
| 4-{17β-Hydroxy- 17α-(1,1,1-trifluoroethoxymethyl)-3-oxoestra-4,9-dien-11β-yl]benzaldehyde-1E-oxime | 177 | 94 | 3.0 |
| Ru 38 486 (Reference) | 685 | 506 | 3.0 |

EXAMPLE 1

4-[17β-Hydroxy-17α-(methoxymethyl)-3-oxoestra-4,9-dien-11β-yl]benzaldehyde-1E-oxime (Ia)

33 g of 4-[17β-hydroxy-17α-(methoxymethyl)-3-oxoestra-4,9-dien-11β-yl]benzaldehyde (VIIa) is dissolved under argon in 250 ml of pyridine and mixed with 5.8 g of hydroxylamine hydrochloride. After 2 hours, it is stirred into ice water, the precipitate is suctioned off, washed and dried. The crude product (40 g) is purified by chromatography on silica gel. 20 g of 4-[17β-hydroxy-(17α-(methoxymethyl)-3-oxoestra-4,9-dien-11β-yl]benzaldehyde-1E-oxime (Ia) [Melting point: 135 to 145° C. (EtOH/water); $α_D$=+236° (CHCl$_3$); $^1$H-NMR: 9.00 (s, 1H, NOH), 8.11 (s, 1H, HC═N), 7.45 (d, 2H, J=8.2, H-3'), 7.17 (d, 2H, J=8.2, H-2'), 5.79 (s, 1H, H-4), 4.38 (d, 1H, J=7.1, H-11), 3.58 (d, 2H, J=9.0, CH$_2$O), 3.43 (s, 3H, OCH$_3$), 3.25 (d, 2H, J=9.0, CH$_2$O), 0.48 (s, 3H, H-18)], and 1.5 g of 4-[17β-hydroxy-17α-(methoxymethyl)-3-oxoestra-4,9-dien-11β-yl]benzaldehyde-1Z-oxime (Ib) [melting point 135 to 146° C. (acetone); $α_D$=+192°; $^1$H-NMR: 8.56 (s, 1H, NOH), 7.86 (d, 2H, J=8.4, H-3'), 7.33 (s, 1H, HC═N), 7.26 (d, 2H, J=8.4, H-2'), 5.79 (s, 1H, H-4), 4.41 (d, 1H, J=7.2, H-11), 3.57 (d, 2H, J=9.1, CH$_2$O), 3.42 (s, 3H, OCH$_3$), 3.23 (d, 2H, J=9.1, CH$_2$O), 0.54 (s, 3H, H-18) are obtained.

PRODUCTION OF THE STARTING COMPOUND

Stage 1

3,3-Dimethoxy-estra-5(10),9(11)-diene-17(S)-spiro-1',2'-oxiranes (Xa)

12 g of 3,3-Dimethoxy-estra-5(10), 9(11)-dien-17-one (Ixa) and 9 g of trimethylsulfonium iodide in 60 ml of dimethylformamide are mixed while being stirred and while being cooled slightly with 5.5 g of potassium-tert.-butylate. After 60 minutes, 50 ml of n-hexane and 30 ml of water are added, the phases are separated, and the organic phase is washed with water. The solution is dried with sodium sulfate and concentrated by evaporation in a vacuum until crystallization occurs. The recrystallization is carried out from n-hexane.

Yield: 11 g. Melting point 94 to 97° C.; $\alpha_D$=+164° (CHCl$_3$); $^1$H-NMR ($\delta$, ppm, 300 MHz, CDCl$_3$/TMS): 5.51 (d, J=5.6 Hz, H-11), 3.24 (s, 3H, OCH$_3$), 3.23 (s, 3H, OCH$_3$), 2.93 (d, 1H, J=5.0 Hz, H-20), 2.66 (d, 1H, J=5.0 Hz, H-20), 0.87 (s, 2H, H-18).

Stage 2

3,3-Dimethoxy-17α-(methoxymethyl)-estra-5(10),9(11)-dien-17β-ol (XIa).

11 g of the 3,3-dimethoxy-estra-5(10),9(11)-diene-17(S)-spiro-1',2'-oxiranes (Xa) is suspended in 40 ml of methanol and mixed with 40 ml of 3N sodium methylate solution and refluxed for 2 hours. After water is added, the methanol is distilled off, extracted with tert.-butyl methyl ether and concentrated by evaporation. The recrystallization is carried out from an ethanol/water mixture. Melting point 73 to 76° C.; $\alpha_D$=+135° (CHCl$_3$); $^1$H-NMR ($\delta$, ppm), 5.56 (m, 1H, H-11), 3.47 (d, 1H, J=9.1 Hz, OCH$_2$), 3.37 (s, 3H, CH$_2$OCH$_3$), 3.24 (s, 3H, 3-OCH$_3$), 3.23 (s, 3H, 3-OCH$_3$), 3.20 (d, 1H, J=9.1 Hz, OCH$_2$), 0.88 (s, 3H, H-18).

Stage 3

3,3-Dimethoxy-5α,10α-epoxy-17α-(methoxymethyl)-estr-9(11)-en-17β-ol and 3,3-Dimethoxy-5β,10β-epoxy-17α-(methoxymethyl)-estr-9(11)-en-17β-ol (XIIa):

4.2 ml of pyridine, 3.75 ml of hexafluoroacetone-sesquihydrate and 37.5 ml of 50% hydrogen peroxide solution are added in succession to a solution of 30 g (XIa) in 300 ml of methylene chloride. After 4 hours at room temperature, sodium thiosulfate solution is added, the phases are separated, the organic phase is washed with sodium bicarbonate solution and water, dried, and the solvent is evaporated in a vacuum. 31 g of crude product (XIIa), which is used directly in the Grignard reaction, is obtained.

Stage 4

4-[(3,3-Dimethoxy)-5α,17βdihydroxy-17α-(methoxymethyl)-estr-9-en-11α,β-yl]benzaldehyde-dimethyl ketal (XIIIa):

4.5 g of copper(I) chloride is added at −35° C. to a Grignard solution that is produced from 7.6 g of magnesium, and 72 g of 4-bromobenzaldehyde-dimethyl ketal in 100 ml of THF. It is stirred for 20 minutes at this temperature, and then a solution of 28 g of epoxide mixture (XIIa) in 70 ml of THF is added in drops. Then, it is allowed to heat to room temperature, mixed with aqueous ammonium chloride solution, and the steroid is extracted with ethyl acetate, the organic phase is washed neutral, it is dried and concentrated by evaporation in a vacuum. The crude product (XIIIa) is used directly in the next stage.

Stage 5

4-[17β-Hydroxy-17α-(methoxymethyl)-3-oxoestra-4,9-dien-11β-yl]benzaldehyde (IVXa):

75 g of crude product (XIIIa) is dissolved in 250 ml of 70% acetic acid and stirred under argon for 2 hours at 50° C. It is cooled, methylene chloride is added, the phases are separated, washed neutral, methyl-tert-butyl ether is added, and the organic phase is concentrated by evaporation in a vacuum. 24 g of a pale yellow crude product (XIVa), which contains only a small portion of the 11α-benzaldehyde, is obtained.

Stage 6

4-[17β-Hydroxy-17α-(methoxymethyl)-3-oxoestra-4,9-dien-11β-yl]benzaldehyde (VIIa):

24 g of crude product (XIVa) is dissolved in methylene chloride, mixed with tert.-butyl methyl ether and concentrated by evaporation in a vacuum. In this case, the pure 11β-benzaldehyde (VIIa) precipitates in crystalline form, which again is recrystallized in ethyl acetate.

Melting point 235 to 240° C.; $\alpha_D$=+209° (CHCl$_3$); $^1$H-NMR: 9.97 (s, 1H, CHO), 7.80 (d, 2H, J=8.1, H-3'), 7.38 (d, 2H, J=8.1, H-2'), 5.80 (s, 1H, H-4), 4.45 (d, 1H, J=7.5, H-11), 3.57 (d, 2H, J=9.2, CH$_2$O), 3.42 (d, 2H, J=10.8, CH$_2$O), 3.41 (s, 3H, OCH$_3$), 0.51 (s, 3H, H-18).

EXAMPLE 2

4-[17β-Methoxy-17α-(methoxymethyl)-3-oxoestra-4,9-dien-11β-yl] benzaldehyde-1E-oxime (Ic)

1.75 g of hydroxylamine hydrochloride is added to a solution of 10 g of (VIIb) in 100 ml of pyridine at room temperature, and the mixture is stirred for 2 hours. It is poured into ice water, the precipitate is suctioned off, dried on calcium chloride, and the crude product is chromatographed on silica gel. 7 g of 4-[17β-methoxy-17α-(methoxymethyl)-3 -oxoestra-4,9-dien-11β-yl]benzaldehyde-1E-oxime (Ic) [melting point 196-198° C. (EtOH/H$_2$O); $\alpha_D$=+220° (CHCl$_3$); $^1$H-NMR: 8.38 (s, 1H, NOH), 8.10 (s, 1H, HC=N), 7.47 (d, 2H, J=8.1, H-3'), 7.20 (d, 2H, J=8.1, H-2'), 5.79 (s, 1H, H-4), 4.38 (d, 1H, J=7.3, H-11), 3.58 (d, 2H, J=10.8, CH$_2$O), 3.41 (s, 3H, OCH$_3$), 3.41 (d, 2H, J=10.8, CH$_2$O), 3.25 (s, 3H, OCH$_3$), 0.54 (s, 3H, H-18)] and 300 mg of 4-[17β-methoxy-17α-(methoxymethyl)-3-oxoestra-4,9-dien-11β-yl]benzaldehyde-1Z-oxime (Id) [melting point 120-138° C. (acetone/n-hexane); $\alpha_D$=+217° (CHCl$_3$); $^1$H-NMR: 9.38 (s, 1H, NOH), 7.88 (d, 2H, J=8.9, H-3'), 7.33 (s, 1H, HC=N), 7.26 (d, 2H, J=8.9, H-2'), 5.79 (s, 1H, H-4), 4.39 (d, 1H, J=7.3, H-11), 3.58 (d, 2H, J=10.5, CH$_2$O), 3.42 (d, 2H, J=10.5, CH$_2$O), 3.41 (s, 3H, OCH$_3$), 3.26 (s, 3H, OCH$_3$), 0.54 (s, 3H, H-18) are obtained.

PRODUCTION OF THE STARTING COMPOUND

Stage 1

3,3,17β-Trimethoxy-17α-(methoxymethyl)-estra-5(10,9(11)-diene (XIb)

12 g of (XIa), 5 ml of methyl iodide and 10 g of potassium-tert.-butylate are stirred in 80 ml of tert.-butyl methyl ether for 4 hours at 30° C. to 40° C. After water is added, the phase separation is carried out, the organic phase is washed with water, dried and concentrated by evaporation. The crude product (XIb) is recrystallized in methanol.
Melting point 95 to 97° C. (MeOH); $\alpha_D$=+146°(CHCl$_3$); $^1$H-NMR (δ, ppm): 5.52 (m, 1H, H-11), 3.63 (d, 1H, J=10.7 Hz, OCH$_2$), 3.38 (s, 3H, CH$_2$OCH$_3$), 3.31 (d, 1H, J=10.7 Hz, OCH$_2$), 3.29 (s, 3H, 17β-OCH$_3$), 3.24 (s, 3H, 3-OCH$_3$), 3.23 (s, 3H, 3-OCH$_3$), 0.88 (s, 3H, H-18).

Stage 2

17α-(Methoxymethyl)-3,3,17β-trimethoxy-5≠,10α-epoxy-estr-9(11)-ene and 17α-(Methoxymethyl)-3,3,17β-trimethoxy-5β,10β-epoxy-estr-9(11)-ene (XIIb):

0.3 ml of pyridine and 0.25 ml of hexafluoroacetone-sesquihydrate are added to 2 g of (XIb) in 20 ml of methylene chloride. At room temperature, 2.5 ml of hydrogen peroxide is added in drops, after 4 hours sodium sulfite solution is added, the phases are separated, and the organic phase is washed with sodium bicarbonate and water, dried on sodium sulfate and vacuum-evaporated. The epoxide mixture (XINb) is used directly in the next stage.

Stage 3

11α,β-4-[17α-(Methoxymethyl)-3,3,17β-trimethoxy-5α-hydroxy-estr-9-en-11β-yl]benzaldehyde-dimethyl ketal (XIIIb)

60 mg of copper(I) chloride is added at −35° C. to a Grignard solution that is produced from 2.4 g of 4-bromobenzaldehyde dimethyl ketal, and 0.2 g of magnesium in 20 ml of THF. It is stirred for 20 minutes at this temperature, and a solution of 1 g (XIIb) in 5 ml of THF is added in drops. Then, the reaction is allowed to reach room temperature, the batch is decomposed with aqueous ammonium chloride solution, the solution is extracted with ethyl acetate, and the organic phase is washed with water; it is dried with sodium sulfate and concentrated by evaporation. The crude product (XIIIb) (1.5 g) is used directly in the next stage.

Stage 4

4-[17β-Methoxy-17α-(methoxymethyl)-3-oxoestra-4,9-dien-11β-yl]benzaldehyde VIIb):

1.5 g of crude product (XIIIb) is dissolved in 20 ml of acetone and mixed with 180 mg of p-toluenesulfonic acid. After 1 hour, it is neutralized with aqueous ammonia and diluted with water. In this case, the aldehyde mixture, which is recrystallized from acetone, precipitates. 0.7 g of 4-[17β-methoxy-17α-methoxymethyl)-3-oxoestra-4,9-dien-11β-yl] benzaldehyde (VIIb) is obtained. Melting point 245 to 250° C. (acetone); $\alpha_D$=+193° (CHCl$_3$); $^1$H-NMR: 9.97 (s, 1H, CHO), 7.79 (d, 2H, J=8.1, H-3'), 7.37 (d, 2H, J=8.1, H-2'), 5.79 (s, 1H, H-4), 4.44 (d, 1H, J=7.5, H-11), 3.56 (d, 2H, J=10.8, CH$_2$O), 3.42 (d, 2H, J=10.8, CH$_2$O), 3.41 (s, 3H, OCH$_3$), 3.25 (s, 3H, OCH$_3$), 0.51 (s, 3H, H-18).

EXAMPLE 3

4-[17β-Ethoxy-17α-(methoxymethyl)-3-oxoestra-4,9-dien-11β-yl]benzaldehyde-1E-oxime (Ie)

1.7 g of (VIIc) is stirred in 25 ml of pyridine with 250 mg of hydroxylamine hydrochloride for 1 hour at room temperature. Then, it is poured into 100 ml of ice water, the precipitate is suctioned off, washed neutral with water and dried with calcium chloride. The crude product (1.7 g) is purified by chromatography on silica gel. 890 mg of (Ie) is obtained. Melting point 184 to 187° C. (acetone/hexane); $\alpha_D$=+214° (CHCl$_3$); $^1$H-NMR: 9.10 (s, 1H, CH=N), 7.58 (s, 1H, OH), 7.49 (d, 2H, J=8.4, H-3'), 7.21 (d, 2H, J=8.4, H-2'), 5.78 (s, 1H, H-4), 4.38 (d, 1H, J=6.9, H-11), 3.62 (d, 2H, J=10.8, CH$_2$O), 3.40 (s, 3H, OCH$_3$), 3.36 (d, 2H, J=10.8, CH$_2$O), 1.11 (t, 3H, CH$_2$CH$_3$), 0.54 (s, 3H, H-18).

PRODUCTION OF THE STARTING COMPOUND

Stage 1

3,3,-Dimethoxy-17α-(methoxymethyl)-estra-5(10),9(11)-diene-17β-ethoxy Methyl Ether (XIc)

4.2 g of (XIa) is reacted with 15.6 g of potassium-tert-butanolate and 76 ml of iodoethane in 400 ml of toluene at 35° C. within 14 hours. After water is added, the phases are separated, the organic phase is worked up in a neutral manner, and the solvent is vacuum-evaporated after drying. The crude product (XIc) is used directly in the next stage without purification.

Stage 2

3,3,-Dimethoxy-5α,10α-epoxy-17α-(methoxymethyl)-estra-5(10),9(11)-diene-17β-ethoxy Methyl Ether and 3,3,-Dimethoxy-5β,10βepoxy-17α-(methoxymethyl)-estra-5(10),9(11)-diene-17β-ethoxy Methyl Ether (XIIc)

0.5 ml of pyridine and 0.4 ml of hexafluoroacetone-sesquihydrate are added to 3.3 g of (XIc) in 20 ml of methylene chloride. At room temperature, 4.5 ml of hydrogen peroxide is added in drops, and after 4 hours, sodium sulfite solution is added, the phases are separated, and the organic phase is washed with sodium bicarbonate and water, dried on sodium sulfate and vacuum-evaporated. The epoxide mixture (XIIc) is used directly in the next stage.

Stage 3

4-[3,3-Dimethoxy-17β-ethoxy-5α-hydroxy-17α-(methoxymethyl)-estr-9-en-11α,β-yl]benzaldehyde-1,1-dimethyl Ketal (XIIIc)

60 mg of copper(I) chloride is added at −35° C. to a Grignard solution that is produced from 4.0 g of 4-bromobenzaldehyde dimethyl ketal, and 0.3 g of magnesium in 20 ml of THF. It is stirred for 20 minutes at this temperature, and a solution of 2 g of (XIIc) in 5 ml of THF is added in drops. The reaction is then allowed to reach room temperature, the batch is decomposed with aqueous ammonium chloride solution, the solution is extracted with ethyl acetate, and the organic phase is washed with water; it is dried with sodium sulfate and concentrated by evaporation in a vacuum. The crude product (XIIIc) (4.5 g) is used directly in the next stage.

Stage 4

4-[17β-Ethoxy-17α-(methoxymethyl)-3-oxoestra-4,9-dien-11β-yl]benzaldehyde (VIIc):

2.8 g of (XIIIc) is dissolved in 40 ml of acetone. After 1.0 ml of water is added, 1.4 g of p-toluenesulfonic acid is added, and after 1 hour, ice water is added. The (VIIc) that precipitates in this case is suctioned off, dried and recrystallized in acetone/hexane and again in tert-butyl methyl ether.

Melting point 164 to 167° C.; $\alpha_D$=+199° (CHCl$_3$); $^1$H-NMR: 9.97 (s, 1H, CHO), 7.80 (d, 2H, J=8.1, H-3'), 7.37 (d, 2H, J=8.1, H-2'), 5.79 (s, 1H, H4), 4.43 (d, 1H, J=7.5, H-11), 3.58 (d, 2H, J=10.8, CH$_2$O), 3.41 (m, 2H, CH$_2$O), 3.40 (s, 3H, OCH$_3$), 1.10 (t, 3H, ethyl), 0.51 (s, 3H, H-18).

EXAMPLE 4

4-[17β-Methoxy-17α-(ethoxymethyl)-3-oxoestra-4,9-dien-11β-yl]benzaldehyde-1E-oxime The production is carried out analogously to Example 2.
Melting point 90-95° C. (tert.-butyl methyl ether) $\alpha_D$=+1770 (CHCl$_3$); $^1$HNMR: 8.10 (s, 1H, HC=N), 7.60 (s, 1H, NOH), 7.48 (d, 2H, J=8.1, H-3'), 7.20 (d, 2H, J=8.1, H-2'), 5.78 (s, 1H, H4), 4.36 (d, 1H, J=7.3, H-11), 3.61 (d, 2H, J=10.8, CH$_2$O), 3.42 (d, 2H, J=10.8, CH$_2$O), 3.26 (s, 3H, OCH$_3$), 1.27 (t, 3H, ethyl), 0.53 (s, 3H, H-18)

EXAMPLE 5

4-[17β-Hydroxy-17α-(ethoxymethyl)-3-oxoestra-4,9-dien-11β-yl]benzaldehyde-1E-oxime The production is carried out analogously to Example 1.
Foam (hexane); $\alpha_D$=+226° (CHCl$_3$); $^1$H-NMR: 8.10 (s, 1H, HC=N), 7.70 (s, 1H, NOH), 7.48 (d, 2H, J=8.1, H-3'), 7.20 (d, 2H, J=8.1, H-2'), 5.78 (s, 1H, H-4), 4.38 (d, 1H, J=7.2, H-11), 3.61 (d, 2H, J=10.8, CH$_2$O), 3.23 (d, 2H, J=10.8, CH$_2$O), 3.26 (s, 3H, OCH$_3$), 1.25 (t, 3H, ethyl), 0.52 (s, 3H, H-18)

EXAMPLE 6

4-[17β-Methoxy-(17α-(isopropyloxymethyl)-3-oxoestra-4,9-dien-11β-yl] benzaldehyde-1E-oxime The production is carried out analogously to Example 1.
Melting point 192-196° C. decomposition. (Diethyl ether); $\alpha_D$=+215° (CHCl$_3$);
$^1$H-NMR: 8.10 (s, 1H, HC=N), 8.07 (s, 1H, NOH), 7.47 (d, 2H, J=8.1, H-3'), 7.19 (d, 2H, J=8.1, H-2'), 5.79 (s, 1H, H-4), 4.38 (d, 1H, J=6.9, H-11), 3.62 (d, 2H, J=10.8, CH$_2$O), 3.22 (d, 2H, J=10.8, CH$_2$O), 3.02 (s, 1H, OH), 1.22 (m, 6H, isopropyl), 0.52 (s, 3H, H-18)

EXAMPLE 7

4-[17β-Hydroxy-(17α-(isopropyloxymethyl)-3-oxoestra-4,9-dien-11β-yl]benzaldehyde-1E-oxime The production is carried out analogously to Example 2.
Melting point 143° C. decomposition. (acetone/n-hexane); $\alpha_D$=+199°(CHCl$_3$);
$^1$H-NMR: 8.10 (s, 1H, HC=N), 8.00 (s, 1H, NOH), 7.48 (d, 2H, J=8.4, H-3'), 7.21 (d, 2H, J=8.4, H-2'), 5.79 (s, 1H, H-4), 4.37 (d, 1H, J=6.9, H-11), 3.61 (d, 2H, J=10.5, CH$_2$O), 3.43 (d, 2H, J=10.8, CH$_2$O), 3.26 (s, 3H, OCH$_3$), 1.22 (t, 6H, 6.0 isopropyl), 0.54 (s, 3H, H-18)

EXAMPLE 8

4-[17β-Hydroxy-(17α-(ethylthiomethyl)-3-oxoestra-4,9-dien-11β-yl]benzaldehyde-1E-oxime The production is carried out analogously to Example 1.
Melting point 132 to 137° C. (acetone); $\alpha_D$=+165° (CHCl$_3$); $^1$H-NMR: 8.10 (s, 1H, HC=N), 7.93 (s, 1H, NOH), 7.49 (d, 2H, J=8.4, H-3'), 7.20 (d, 2H, J=8.4, H-2'), 5.79 (s, 1H, H4), 4.42 (d, 1H, J=7.2, H-11), 2.96 (d, 2H, J=13.2, CH$_2$S), 2.90 (s,1H,OH), 2.70 (d, 2H, J=12.9, CH$_2$S), 1.29 (t, 3H, 10.2, SCH$_2$CH$_3$), 0.56 (s, 3H, H18)

EXAMPLE 9

4-[17β-Hydroxy-(17α-(1,1,1-trifluoroethoxymethyl)-3-oxoestra-4,9-dien-11β-yl]benzaldehyde-1E-oxime The production is carried out analogously to Example 1.
Melting point 132 to 136° C. (diethyl ether), $\alpha_D$=+182° (CHCl$_3$); $^1$H-NMR: 8.11 (s, 1H, HC=N), 7.60 (s, 1H, NOH), 7.49 (d, 2H, J=8.4, H-3'), 7.20 (d, 2H, J=8.1, H2'), 5.79 (s, 1H, H-4), 4.41 (d, 1H, J=7.2, H-11), 3.93 (m, 2H, CH$_2$CH$_3$), 3.82 (d, 2H, J=9.0, CH$_2$O), 3.50 (m, CH$_2$CF$_3$+ OH), 0.55 (s, 3H, H-18)

The invention claimed is:
1. A process for preparing a 4-(17α-methyl-substituted 3-oxoestra-4,9-dien-11β-yl) benzaldehyde-(1E or 1Z)-oxime of formula (I)

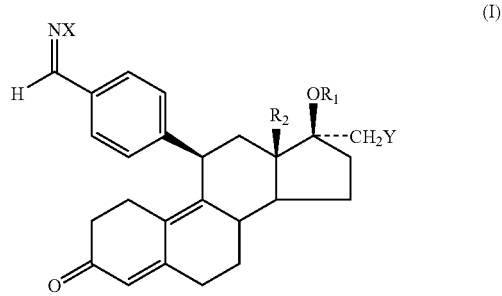

in which
R$_1$ is a hydrogen atom, a C$_{1-6}$-alkyl radical or a C$_n$F$_{2n+1}$ radical,
R$_2$ is a C$_{1-4}$-alkyl radical or a trifluoromethyl group,
X is an OH group in E- or Z-position,
Y is an OC$_{1-6}$-alkyl group, an SC$_{1-6}$-alkyl group or an OCH$_2$C$_n$F$_{2n+1}$ group, and
n is 1, 2 or 3, comprising converting a 3,3-dimethoxy-estra-5(10),9(11)-en-17-one compound of formula (IX)

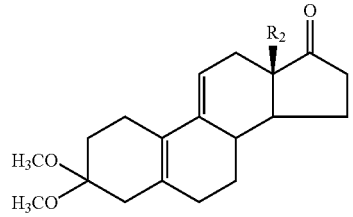

(IX)

in which

R$_2$ is a C$_{1-4}$-alkyl radical or a trifluoromethyl group, with an active methylene reagent in an inert solvent into a spiroepoxide compound of formula (X)

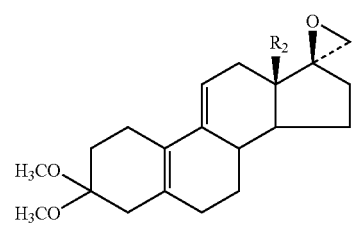

(X)

in which

R$_2$ is a C$_{1-4}$-alkyl radical or a trifluoromethyl group, cleaving the 17-spiroepoxy group of the compound of formula (X) with an alkali or alkaline-earth alcoholate, alkali or alkaline-earth thiol alcoholate or a trifluoroalkyl alcohol and potassium-tert-butanolate in an inert solvent, and forming a 17α-CH$_2$Y compound of formula (XI)

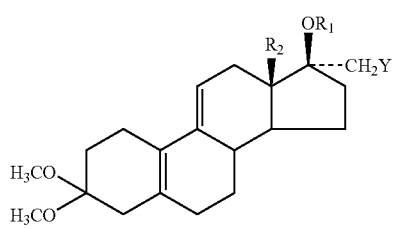

(XI)

in which

R$_1$ is a hydrogen atom,

R$_2$ is a C$_{1-4}$-alkyl radical or a trifluoromethyl group, and

Y is an OC$_{1-6}$-alkyl group, an SC$_{1-6}$-alkyl group or an OCH$_2$C$_n$F$_{2n+1}$ group, optionally reacting the 17β-hydroxyl group of the compound of formula (XI) with an alkyl halide or fluoroalkyl iodide in the presence of a strong base in an inert solvent to form a 17β-ether of formula (XI''),

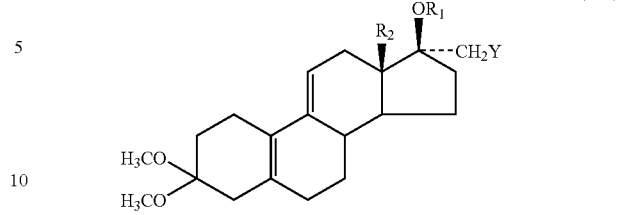

(XI'')

in which

R$_1$ is a C$_{1-6}$-alkyl radical or a C$_n$F$_{2n+1}$ radical,

R$_2$ is a C$_{1-4}$-alkyl radical or a trifluoromethyl group, and

Y is an OC$_{1-6}$-alkyl group, an SC$_{1-6}$-alkyl group or an OCH$_2$C$_n$F$_{2n+1}$ group, epoxidizing the compound of formula (XI) or (XI'') on the 5(10)-double bond thereof, producing a mixture of 5α, 10α-epoxy- and 5β, 10β-epoxy-17α-methyl-substituted estr-9(11)-ene-3,3-dimethyl ketals of formula (XII)

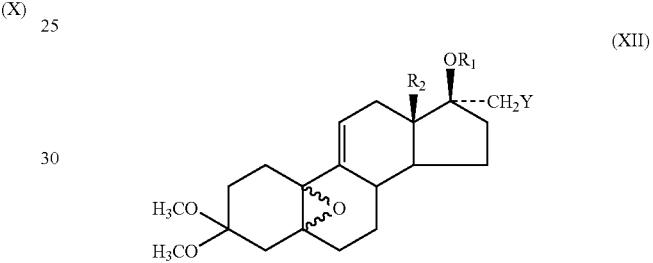

(XII)

in which

R$_1$ is a hydrogen atom, a C$_{1-6}$-alkyl radical or a C$_n$F$_{2n+1}$ radical, R$_2$ is a C$_{1-4}$-alkyl radical or a trifluoromethyl group, and Y is an OC$_{1-6}$-alkyl group, an SC$_{1-6}$-alkyl group or an OCH$_2$C$_n$F$_{2n+1}$ group, reacting the compound of formula (XII) with a 4-bromobenzaldehyde ketal, magnesium and Cu(I)Cl at a temperature of between −35°C. and room temperature form a 3,3-dimethoxy-5α-hydroxy-17α-methyl-substituted 11α,β-benzaldehydedimethyl ketal of formula (XIII)

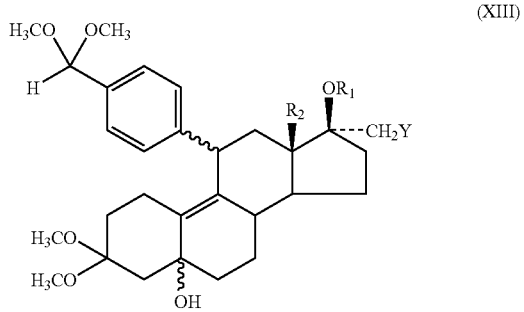

(XIII)

in which

R$_1$ is a hydrogen atom, a C$_{1-6}$-alkyl radical or a C$_n$F$_{2n+1}$ radical, R$_2$ is a C$_{1-4}$-alkyl radical or a trifluoromethyl group, and Y is an $OC_{1-6}$-alkyl group, an $SC_{1-6}$-alkyl group or an $OCH_2C_nF_{2n+1}$ group, subjecting the compound of formula (XIII) to acid hydrolysis to cleave any protective groups, to form a mixture of 11α,β-benzaldehyde compounds of formula (XIV)

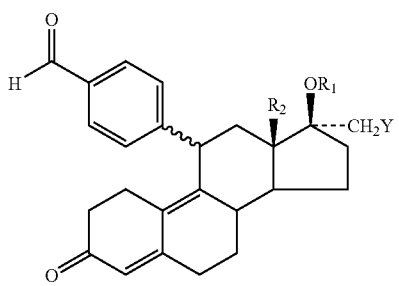

(XIV)

in which

R$_1$ is a hydrogen atom, a $C_{1-6}$-alkyl radical or a $C_nF_{2n+1}$ radical,

R$_2$ is a $C_{1-4}$-alkyl radical or a trifluoromethyl group, and

Y is an $OC_{1-6}$-alkyl group, an $SC_{1-6}$-alkyl group or an $OCH_2C_nF_{2n+1}$ group, isolating by crystallizing a pure 11β-benzaldehyde compound, and converting the aldehyde function of said 11β-benzaldehyde compound by a hydroxylammonium salt in the presence of a base at room temperature into a mixture of E/Z-benzaldoximes of formula (I).

2. A process according to claim 1, further comprising separating the mixture of the E/Z-benzaldoximes of formula (I) into E or Z-benzaldoximes by recrystallization and/or by chromatography.

3. A process according to claim 1, wherein R$_1$ is a $C_{1-3}$-alkyl radical.

4. A process according to claim 1, wherein R$_2$ is a $C_{1-3}$-alkyl radical.

5. A process according to claim 1, wherein Y is an $OC_{1-3}$-alkyl radical or an $SC_{1-3}$-alkyl radical.

6. A process according to claim 1, wherein

4-[17β-Hydroxy-17α-(methoxymethyl)-3-oxoestra-4,9-dien-11β-yl]benzaldehyde-1E-oxime, 4-[17β-Hydroxy-17α-(methoxymethyl)-3-oxoestra-4,9-dien-11β-yl]benzaldehyde-1Z-oxime, 4-[17β-Methoxy-17α-(methoxymethyl)-3-oxoestra-4,9-dien-11β-yl]benzaldehyde-1E-oxime, 4-[17β-Methoxy-17α-(methoxymethyl)-3-oxoestra-4,9-dien-11β-yl]benz-aldehyde-1Z-oxime, 4-[17β-Ethoxy-(17α-(methoxymethyl)-3-oxoestra-4,9-dien-11β-yl]benzaldehyde-1E-oxime, 4-[17β-Hydroxy-17α-(ethoxymethyl)-3-oxoestra-4,9-dien-11β-yl]benzaldehyde-1E-oxime, 4-[17β-Methoxy-17α-(ethoxymethyl)-3-oxoestra-4,9-dien-11β-yl]benzaldehyde-1E-oxime, 4-[17β-Hydroxy-17α-(isopropyloxymethyl)-3-oxoestra-4,9-dien-11β-yl]benzaldehyde-1E-oxime, 4-[17β-Methoxy-17α-(isopropyloxymethyl)-3-oxoestra-4,9-dien-11β-yl]benzaldehyde-1E-oxime, 4-[17β-Hydroxy-17α-(ethylthiomethyl)-3-oxoestra-4,9-dien-11β-yl]benzaldehyde-1E-oxime, or 4-{17β-Hydroxy-17α-(1,1,1-trifluoroethoxymethyl)-3-oxoestra-4,9-dien-11β-yl]benzaldehyde-1E-oxime is prepared.

7. A process according to claim 1, wherein R$_1$ is a methyl group or a trifluoromethyl group.

8. A process according to claim 1, wherein R$_2$ is a methyl group or a trifluoromethyl group.

9. A process according to claim 1, wherein Y is a methoxy, ethoxy, isopropyloxy, methylthio, ethylthio, or trifluoroethoxy group.

10. A process according to claim 1, wherein R$_2$ is a methyl group.

11. A process according to claim 1, wherein R$_2$ is a $C_{1-4}$-alkyl radical.

12. A process according to claim 1, wherein Y is a methoxy, ethoxy, isopropyloxy, methylthio, or ethylthio group.

13. A process according to claim 1, wherein the isolated 11β-benzaldehyde compound is a compound of the following formula

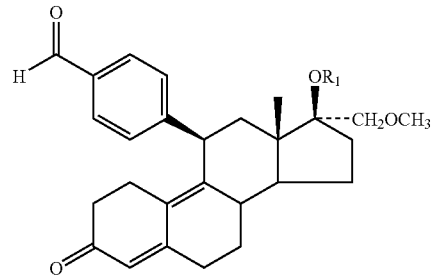

wherein R$_1$ is a hydrogen atom or a $C_{1-6}$-alkyl radical.

14. A compound of formula (I),

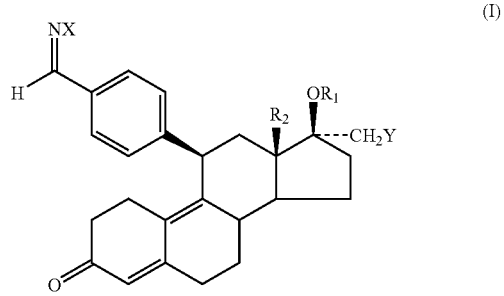

(I)

wherein

R$_1$ is a $C_nF_{2n+1}$ radical, n is 1, 2 or 3,

R$_2$ is a $C_{1-4}$-alkyl radical or a trifluoromethyl group,

X is an OH group in E- or Z-position, and

Y is an $OC_{1-6}$alkyl group, an $SC_{1-6}$-alkyl group or an $OCH_2C_nF_{2n+1}$ group.

15. A compound of formula (I),

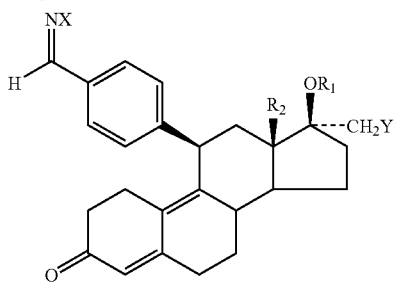

wherein
Y is an $OCH_2C_nF_{2n+1}$ group,
n is 1, 2 or 3,
$R_1$ is a hydrogen atom, a $C_{1-6}$-alkyl radical or a $C_nF_{2n+1}$ radical,
$R_2$ is a $C_{1-4}$-alkyl radical or a trifluoromethyl group, and
X is an OH group in E- or Z-position.

16. A compound according to claim 14, wherein $R_2$ is a $C_{1-4}$-alkyl radical.

17. A compound according to claim 15, wherein $R_2$ is a $C_{1-4}$-alkyl radical.

18. A compound according to claim 15, wherein $R_1$ is a $C_{1-6}$-alkyl radical or a $C_nF_{2n+1}$ radical.

19. A compound according to claim 14, wherein n is 1.

20. A compound according to claim 15, wherein n is 1.

* * * * *